United States Patent [19]

McDaniel, Jr. et al.

[11] Patent Number: 4,562,260

[45] Date of Patent: Dec. 31, 1985

[54] PREPARATION OF 1,3,4-THIADIAZOLE-5-SULFONAMIDES

[75] Inventors: Roger L. McDaniel, Jr., Raleigh; Jeffrey W. Portzer; Edward J. Zaiko, both of Cary, all of N.C.

[73] Assignee: Union Carbide Corporation, Danbury, Conn.

[21] Appl. No.: 627,514

[22] Filed: Jul. 3, 1984

[51] Int. Cl.[4] ............................................. C07D 285/12
[52] U.S. Cl. ..................................... 548/141; 548/136; 548/138; 548/142
[58] Field of Search ................ 548/141, 138, 142, 136

[56] References Cited

U.S. PATENT DOCUMENTS

| | | | |
|---|---|---|---|
| 2,820,793 | 1/1958 | Young et al. | 548/141 |
| 2,820,795 | 1/1958 | Young et al. | 548/141 |
| 3,726,892 | 4/1973 | Cebalo | 548/141 |
| 3,824,247 | 7/1974 | Doyle, Jr. et al. | 548/140 |
| 4,021,225 | 5/1977 | Hedrich et al. | 71/90 |

*Primary Examiner*—John Kight
*Assistant Examiner*—Garnette D. Draper
*Attorney, Agent, or Firm*—Clement J. Vicari

[57] ABSTRACT

An improved process for the production of certain 1,3,4-thiadiazole-5-sulfonamides, specifically the precursor to 5-[[(dimethylamino)-carbonyl]methylamino]-N,N-dimethyl-1,3,4-thiadiazole-2-sulfonamide.

16 Claims, No Drawings

PREPARATION OF 1,3,4-THIADIAZOLE-5-SULFONAMIDES

FIELD OF THE INVENTION

This invention relates to an improved process for the production of certain 1,3,4-thiadiazole-5-sulfonamides such as 2-methylamino-1,3,4-thiadiazole-5-N,N-dimethylsulfonamide which is a precursor to 5-[[(dimethylamino)carbonyl]methylamino]-N,N-dimethyl-1,3,4-thiadiazole-2-sulfonamide; an extremely effective herbicide.

BACKGROUND OF THE INVENTION

Certain 1,3,4-thiadiazole-2-sulfonamide compounds can be employed to combat unwanted vegetation both pre- and post-emergently.

Effective compounds have the structural formula

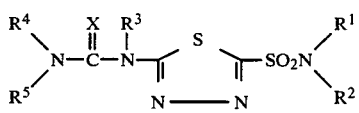

in which $R^1$ and $R^2$ are individually selected from the group consisting of hydrogen, alkyl, alkoxy, cycloalkyl, cyanoalkyl, alkoxyalkyl, alkenyl and alkynyl wherein the alkyl, alkenyl and alkynyl moieties contain from one to six carbon atoms; and heterocyclic structures in which $R^1$ and $R^2$ together form an alkylene or oxyalkylene chain with two to five carbon atoms; $R^3$ is hydrogen or $C_1$–$C_4$ alkyl; $R^4$ is hydrogen or $C_1$ to $C_6$ alkyl; $R^5$ is selected from the group consisting of $C_1$–$C_6$ alkyl, $C_1$–$C_6$ alkenyl, and $C_3$ to $C_6$ cycloalkyl; and X is oxygen or sulfur.

The herbicidal properties of the 1,3,4-thiadiazole-2-sulfonamide structures defined above and various preparatory methods are detailed in U.S. Pat. Nos. 4,021,225 and 3,824,247 which are incorporated herein by reference.

In these patents, although many specific compounds are disclosed having a high degree of phytotoxicity and varied selectivity, it has been recognized that one of the compounds of the disclosed class namely 5-[[dimethylamino)carbonyl]-methylamino]-N,N-dimethyl-1,3,4-thiadiazole-2-sulfonamide, is an unusually effective herbicide of the type which is used industrially to prevent growth of weeds in railroad right-of-ways and in other areas where uncontrolled growth of vegetation is undesirable.

U.S. Pat. No. 4,021,225 recognized that on the basis of disclosures in the chemical literature, particularly Roblin and Clapp, (J. Am. Chem. Soc. 72 4890 (1950), the presence of a free amine function on the thiadiazole molecule precludes the conversion of the mercapto group to the corresponding sulfonyl chloride by oxidative chlorination. Oxidative chlorination is a well known technique, most conveniently operated by introducing chlorine into dilute aqueous hydrochloric acid reaction medium at room temperature or below, with the substance to be chlorinated present in solution or suspension. (See, for example, the publication by Petrow et al. J. Chem. Soc. 198, p. 1508). Amines are known to interfere with the reaction. Consequently a preferred approach to synthesis of the desired class of compounds has involved protection of the free amine group prior to oxidative chlorination, as shown below in the synthesis scheme disclosed in U.S. Pat. No. 4,021,225:

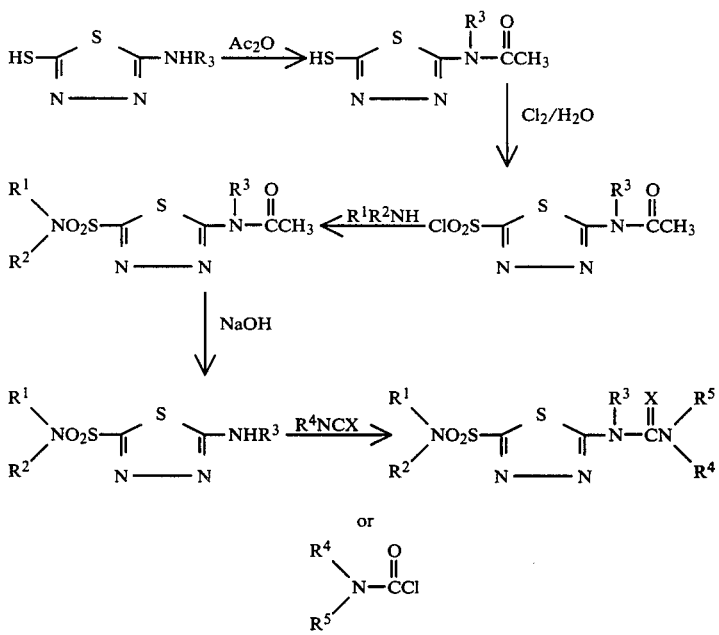

wherein the substituents are as defined above.

U.S. Pat. No. 3,824,247 discloses that protection of the amino substituent on the thiadiazole nucleus is unnecessary in the formation of the corresponding sulfonyl chloride by oxidative chlorination of the mercapto substituent.

Ergo, the more direct preferred route in the prior art to the herbicides of this class is performed in the following sequence:
(a) chlorinating under oxidizing conditions a 2-mercapto-4-amino-1,3,4-thiadiazole to yield a corresponding sulfonyl chloride;

(b) reacting said sulfonyl chloride with a secondary amine to yield a corresponding sulfonamide;

(c) reacting said sulfonamide with a carbamyl chloride or isocyanate or preferably reacting the amine substituent with phosgene in inert solvent followed by reacting the resulting carbamyl chloride with an amine to yield the desired phytotoxic ureido-thiadiazole-sulfonamide as described above.

More specifically, the route to the superior industrial type herbicide 5-[[(dimethylamino)carbonyl]methylamino]-N,N-dimethyl-1,3,4-thiadiazole-2-sulfonamide via the teachings of the '225 patent is as set forth below:

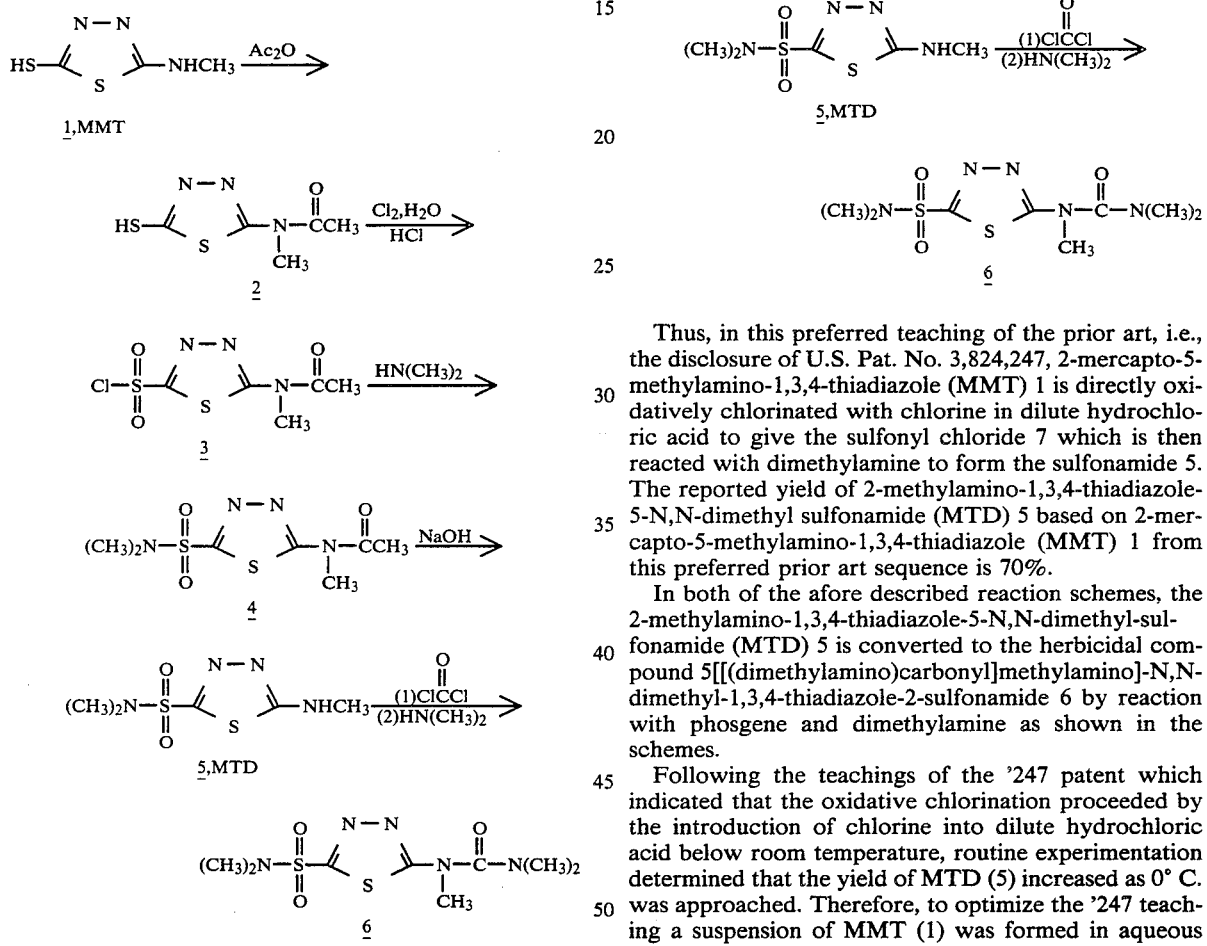

2-mercapto-5-methylamino-1,3,4-thiadiazole (MMT) 1 is converted to the acetyl derivative 2 to protect the methylamino group from the conditions of the subsequent oxidative chlorination. The acetyl derivative 2 is reacted with chlorine in dilute hydrochloric acid to give the sulfonyl chloride 3 which is further reacted with dimethylamine to form the sulfonamide 4. The protecting group is then removed from 4 by reaction with NaOH, resulting in 2-methylamino-1,3,4-thiadiazole-5-N,N-dimethylsulfonamide (MTD) 5.

The improvement disclosed in the '247 patent, based on the discovery that the protecting group was unnecessary and that MMT can be directly oxidatively chlorinated, as specifically applied to the preparation of the above-identified preferred herbicide is shown schematically as follows:

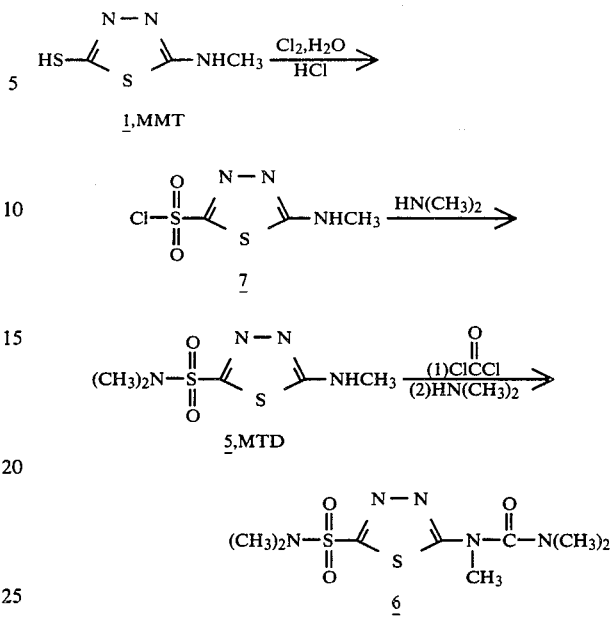

Thus, in this preferred teaching of the prior art, i.e., the disclosure of U.S. Pat. No. 3,824,247, 2-mercapto-5-methylamino-1,3,4-thiadiazole (MMT) 1 is directly oxidatively chlorinated with chlorine in dilute hydrochloric acid to give the sulfonyl chloride 7 which is then reacted with dimethylamine to form the sulfonamide 5. The reported yield of 2-methylamino-1,3,4-thiadiazole-5-N,N-dimethyl sulfonamide (MTD) 5 based on 2-mercapto-5-methylamino-1,3,4-thiadiazole (MMT) 1 from this preferred prior art sequence is 70%.

In both of the afore described reaction schemes, the 2-methylamino-1,3,4-thiadiazole-5-N,N-dimethyl-sulfonamide (MTD) 5 is converted to the herbicidal compound 5[[(dimethylamino)carbonyl]methylamino]-N,N-dimethyl-1,3,4-thiadiazole-2-sulfonamide 6 by reaction with phosgene and dimethylamine as shown in the schemes.

Following the teachings of the '247 patent which indicated that the oxidative chlorination proceeded by the introduction of chlorine into dilute hydrochloric acid below room temperature, routine experimentation determined that the yield of MTD (5) increased as 0° C. was approached. Therefore, to optimize the '247 teaching a suspension of MMT (1) was formed in aqueous sodium chloride solution to prevent the reaction mixture from freezing as the temperature was lowered to 0° C. and below. As the suspension was stirred vigorously, chlorine (3.1 equivalents based on MMT) was introduced into the reaction mixture in test runs conducted at from 0° C. to −12° C. The resulting sulfonyl chloride was converted to MTD by adding sufficient aqueous dimethylamine to neutralize all of the hydrogen chloride as well as to react with the sulfonyl chloride (7 to 9 equivalents of dimethylamine based on MMT).

The absolute yield of MTD (the yield of the crude product multiplied by the product assay) varied inversely with the temperature at which the oxidative chlorination was conducted and ranged from 84% at −12° C. to 37% at 23° C. A Least Squares Linear Regression Analysis of the data revealed that the sensitivity of the yield to temperature was −1.3%/°C.

A temperature of −5° C. is about the lowest practical temperature for large-scale, commercial equipment for this process and the data indicated that a reaction temperature of −5° C. for the oxidative chlorination of MMT from the improved prior art process would result in a 74% absolute yield of MTD.

Utilizing the process discovery of the instant invention, the yields of MTD can be increased and therefore the cost of manufacturing MTD can be made more favorable; ultimately lowering the manufacturing cost of the highly desirable herbicidal compound 5-[(dimethylamine)carbonyl]methylamino]-N,N-dimethyl-1,3,4-thiadiazole-2-sulfonamide.

Accordingly, one or more of the following objectives can be achieved by the practice of this invention. It is an object of this invention to increase the yields of certain 1,3,4-thiadiazole-5-sulfonamides which are useful precursors to herbicidal compounds. Additionally it is an object of this invention to specifically increase the oxidative chlorination yield of 2-methylamino-1,3,4-thiadiazole-5-N,N-dimethyl sulfonamide a precursor in the production of 5-[[(dimethylamino)carbonyl]methylamino]-N,N-dimethyl-1,3,4-thiadiazole-2-sulfonamide; an extremely effective herbicide. Those and other objects will readily became apparent to those skilled in the art in the light of the teachings herein set forth.

SUMMARY OF THE INVENTION

In its broad aspect, this invention relates to the discovery that if a 2-mercapto-5-alkylamino-1,3,4-thiadiazole is added to an aqueous acid and inorganic salt solution simultaneously with a stream of chlorine gas in a given molar ratio and the resulting sulfonyl chloride then reacted with a secondary amine in the usual manner, a significant increase in yield of the respective sulfonamide is realized as well as a favorable increase in the yield/temperature sensitivity ratio. Preferably, said thiadiazole is added as a metal salt in an aqueous solution.

DETAILED DESCRIPTION OF THE INVENTION

As indicated above, the instant invention relates to the discovery of an improved process for the production of certain 1,3,4-thiadiazole-5-sulfonamides and ultimately the production of extremely effective herbicides from these compounds. The invention specifically relates to an improved process for the production of 2-methylamino-1,3,4-thiadiazole-5-N,N-dimethylsulfonamide which is a precursor to 5-[[(dimethylamino)carbonyl]methylamino]-N,N-dimethyl-1,3,4-thiadiazole-2-sulfonamide.

The invention relates to the discovery that if a 2-mercapto-4-amino-1,3,4-thiadiazole is added to an aqueous solution of acid and inorganic salt simultaneously with a stream of chlorine gas to maintain a molar ratio of chlorine to the mercaptan of about 3:1 during the reaction and the resulting sulfonyl chloride subsequently reacted with a dialkyl-amine in the usual manner to achieve the desired 1,3,4-thiadiazole-5-sulfonamide, then significantly increased yields can be achieved over any heretofore realized in the prior art and, in addition, the yield-to-temperature ratio shows decreased sensitivity.

Preferably, to avoid having excess mercaptan present during the oxidative chlorination, i.e., to maintain the molar ratio of about 3:1 of chlorine to the mercaptan during this time, the mercaptan is transformed into a soluble metal salt to enable it to be quantitatively introduced conveniently into the reactor in liquid form.

More specifically, the preferred invention relates to a process for the production of 1,3,4-thiadiazole-5-sulfonamide compounds which comprises: oxidatively chlorinating a metal salt of a compound of formula I

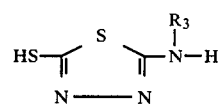

wherein:

$R_3$ is hydrogen or $C_1-C_4$ alkyl by the simultaneous addition of chlorine gas and an aqueous solution of said metal salt in a molar ratio of about 3:1 to an aqueous acid and inorganic salt solution; purging the chlorine gas from the reaction mixture; and sequentially reacting the resulting sulfonyl chloride with from about 7 to 9 equivalents of a secondary amine of the formula II

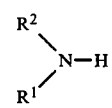

wherein
$R^1$ and $R^2$ are individually selected from the group consisting of hydrogen, alkyl, alkoxy, cycloalkyl, cyanoalkyl, alkoxyalkyl, alkenyl, and alkynyl wherein the alkyl, alkenyl, and alkynyl moieties contain from one to six carbon atoms; and heterocyclic structures in which $R^1$ and $R^2$ together form an alkylene or oxyalkylene chain with two to four carbon atoms to yield a sulfonamide of the following formula III

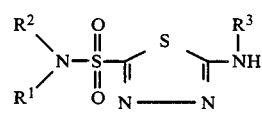

The above sulfonamide can then be reacted with a carbonyl chloride or any isocyanate of the structure formula IV

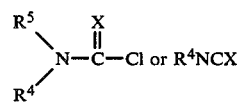

or preferably phosgene in inert solvent followed by reacting the resulting carbamyl chloride with an amine of the formula V

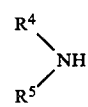

wherein
$R^4$ is hydrogen or $C_1-C_6$ alkyl;
$R^5$ is selected from the group consisting of $C_1-C_6$ alkyl, $C_1-C_6$ alkenyl, and $C_3$ to $C_6$ cycloalkyl; and
X is oxygen or sulfur.

The inorganic salt which is added to the reaction mixture to primarily prevent freezing can be any inorganic salt which has sufficient solubility to provide adequate protection and which is inert to the reaction conditions. The preferred salts are sodium chloride, potassium chloride and calcium chloride.

The acid utilized in the aqueous acidic inorganic salt solution can be any acid which is inert to the reaction conditions and is preferably hydrochloric acid. The preferred cations for the thiadiazole metal salt are sodium and potassium.

The concentration of the metal salt of the 2-mercapto-4-amino-1,3,4-thiadiazole can be any practical value but should not be so high as to have the precipitate hinder effective agitation.

For maximum yields, the chlorine stoichiometry should range from about 2.0 to about 5 molar equivalents per mole of thiadiazole metal salt, preferably from about 2.8 to about 3.8.

The optimum times for the total addition of the thiadiazole metal salt and for the chlorine will vary with the size of the reactor, the degree and type of agitation and the method of cooling. Preferably, the chlorine feed should finish shortly after the thiadiazole salt feed so that an excess of chlorine is not present during the addition period.

The 2-mercapto-4-amino-1,3,4-thiadiazole salt can be prepared by any of the methods known to those skilled in the art. Preferably about 1.3 parts of the 2-mercapto-4-amino-1,3,4-thiadiazole is dissolved in 10 parts of 1.0N sodium hydroxide solution to form the sodium salt solution.

The temperature of the chlorination oxidation reaction can vary from $-30°$ C. to $30°$ C., preferably from $-12°$ C. to $5°$ C.

A general synthesis scheme is detailed below for the production of 2-methylamino-1,3,4-thiadiazole-5-N,N-dimethyl-sulfonamide.

To a reactor is added 10 parts of water, 0.1 part of concentrated HCl, and sodium chloride to prevent freezing. The amount of sodium chloride required depends on the desired reaction temperature. For temperatures down to $-4°$, 1 part of NaCl is sufficient. For temperatures to $-15°$, up to 4 parts of sodium chloride or calcium chloride is required. An aqueous solution of the sodium salt of 2-mercapto-5-methylamino-1,3,4-thiadiazole (MMT) is prepared by dissolving 1.3 parts of MMT in 10 parts of 1.0N NaOH solution. The reactor is cooled to the desired temperature, and the sodium MMT solution is added uniformly over 1 to 3 hours while the contents of the reactor are stirred vigorously. Simultaneously, 2.0 parts (3.2 equivalents) of chlorine gas is introduced under the surface of the reaction mixture uniformly over a period of time slightly longer than that for the sodium MMT feed. When the addition of chlorine is complete, the reaction mixture is sparged with nitrogen for 30 min to remove excess chlorine, and then 40% dimethylamine (7.8 parts, 8 equivalents) is added. The product, 2-methylamino-1,3,4-thiadiazole-5-N,N-dimethylsulfonamide (MTD), is collected by filtration, washed with water, and dried.

Examples 1-6 are illustrative of the prior art procedure for converting MMT to MTD. Examples 7-19 are illustrative of the method of the instant invention.

EXAMPLE 1

To a 5 L jacketed reactor fitted with a mechanical stirrer, a gas dispersion tube extending to near the bottom of the reactor, and a thermometer was charged 75 g (0.51 mols) of 2-mercapto-5-methylamino-1,3,4-thiadiazole (MMT), 1125 mL of water, and 38 g of NaCl. While the temperature of the reactor contents was kept constant at $7°$ by passing coolant through the reactor jacket, 114 g (1.6 mols) of chlorine was added through the gas dispersion tube over 3 hours. After the addition of chlorine was completed, the reaction mixture was purged with a stream of nitrogen for 60 min to remove residual chlorine. Then 450 g of 40% aqueous dimethylamine (4.0 mols) was added rapidly while the temperature was kept below $25°$. After the reaction mixture was stirred for 30 min at $25°$, the product was collected by filtration, washed with water, and dried to give crude 2-methylamino-1,3,4-thiadiazole-5-N,N-dimethylsulfonamide (MTD) as 73.1 g (64.5%) of white solid. By analysis using gas chromatography, this product had a purity of 88.9%; the absolute yield, therefore, was 57.3%.

EXAMPLES 2-6

These experiments employed procedures similar to that described in example 1, except that different temperatures were used during the chlorine addition. The temperatures and the results are shown in Table 1.

TABLE 1

| | Effect of Temp. on Yield of MTD Prior Art Procedures | | | |
|---|---|---|---|---|
| Example | Temp. (°C.) | Crude Yield (%) | Assay (%) | Abs. Yield (%) |
| 1 | 7 | 65 | 89 | 58 |
| 2 | −12 | 92 | 91 | 84 |
| 3 | −2 | 71 | 88 | 62 |
| 4 | −2 | 85 | 87 | 74 |
| 5 | 15 | 52 | 95 | 49 |
| 6 | 23 | 39 | 94 | 37 |

EXAMPLE 7

To a 3 L reactor fitted with a mechanical stirrer, a gas dispersion tube extending to near the bottom of the reactor, a liquid inlet, and a thermometer were charged 563 mL of water, 56 g of NaCl, and 5 mL of concentrated HCl. An aqueous solution of the sodium salt of 2-mercapto-5-methylamino-1,3,4-thiadiazole (MMT) was made by dissolving 75 g (0.5 mol of 98% MMT) in 563 mL of 1.0N NaOH. This sodium MMT solution was added uniformly to the reactor over 1 hour, while simultaneously and with vigorous agitation, 114 g (1.6 mols) of chlorine was added over 1.1 hours through the gas dispersion tube. The temperature of the reaction mixture was kept constant at $-2°$ by passing coolant through the reactor jacket. When the addition of chlorine was completed, the reaction mixture was purged with nitrogen for 30 min., and then 450 g (4.0 mols) of 40% aqueous dimethylamine was added rapidly. The reaction mixture was stirred for 10 min., and then the product was collected by filtration, washed with water, and dried to give 111 g (100%) of crude MTD as a white solid. The product assay by gc analysis was 90%, for an absolute yield of 90%.

EXAMPLES 8-19

These experiments employed procedures similar to that described in example 7. Differences in the reaction conditions, including the temperature during the addition of sodium MMT and chlorine, are summarized in Table 2, which also shows the results.

TABLE 2

| | | | Effect of Temperature on Yield of MTD With MMT Salt Reactants | | | | |
|---|---|---|---|---|---|---|---|
| Example | Salt Type | Salt Grams | Time of Na—MMT feed (hrs) | Temp. (°C.) | Crude Yield (%) | Assay (%) | Absolute Yield (%) |
| 7  | NaCl   | 56  | 1.0 | −2  | 100 | 90 | 90 |
| 8  | CaCl₂  | 245 | 2.5 | −15 | 102 | 94 | 96 |
| 9  | CaCl₂  | 245 | 2.9 | −13 | 99  | 94 | 93 |
| 10 | NaCl   | 200 | 2.1 | −8  | 96  | 91 | 88 |
| 11 | NaCl   | 200 | 2.2 | −6  | 93  | 92 | 86 |
| 12 | NaCl   | 200 | 2.1 | −5  | 97  | 89 | 86 |
| 13 | NaCl   | 56  | 1.9 | −4  | 91  | 92 | 84 |
| 14 | NaCl   | 56  | 2.2 | −3  | 89  | 89 | 80 |
| 15 | NaCl   | 56  | 2.4 | −3  | 97  | 94 | 91 |
| 16 | NaCl   | 56  | 2.0 | −2  | 91  | 93 | 85 |
| 17 | NaCl   | 56  | 2.2 | −2  | 87  | 95 | 83 |
| 18 | NaCl   | 56  | 1.8 | +3  | 93  | 93 | 86 |
| 19 | NaCl   | 56  | 1.7 | +8  | 90  | 90 | 81 |

A Least Squares Linear Regression Analysis of the results of the improved prior art procedure in Examples 1 through 6 showed that the sensitivity of the yield to temperature was −1.3%/°C. whereas the sensitivity of the yield to temperature with the salt reactant procedure of the instant invention as shown in Examples 7 through 19 was −0.6%/°C. Ergo the yields of the instant process are much less sensitive to reaction temperature than the prior art processes.

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:

1. An improvement in a process for the production of certain 2-amino-1,3,4-thiadiazole-5-sulfonamides of the formula:

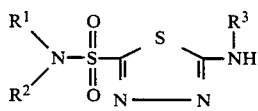

by: (a) oxidatively chlorinating a compound of the formula I:

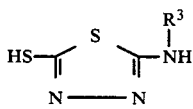

wherein $R_3$ is hydrogen or $C_1$ to $C_4$ alkyl, (b) sequentially reacting the product of the oxidation-chlorination step with a compound of the formula II:

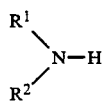

wherein $R^1$ and $R^2$ are individually selected from the group consisting of hydrogen, alkyl, alkoxy, cycloalkyl, cyanoalkyl, alkoxyalkyl, alkenyl and alkynyl wherein the alkyl, alkenyl and alkynyl moieties contain from one to six carbon atoms; and heterocyclic structures in which $R^1$ and $R^2$ together form an alkylene or oxyalkylene chain with two to five carbon atoms, and thereafter isolating the product, the improvement comprising:

(i) performing the oxidative-chlorination step (a) by simultaneously introducing into an aqueous solution of an acid and an inorganic salt, chlorine and a compound of formula I in a molar ratio of chlorine to the said compound of formula I of from about 2 to about 5 at from about −30° C. to 30° C.; and (ii) purging the excess chlorine from the reaction mixture prior to reaction step (b).

2. An improvement in a process for the production of certain 2-amino-1,3,4-thiadiazole-5-sulfonamides of the formula:

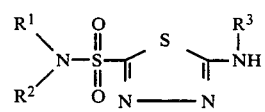

by: (a) oxidatively chlorinating a compound of the formula I:

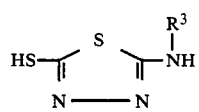

wherein $R_3$ is hydrogen or $C_1$ to $C_4$ alkyl, (b) sequentially reacting the product of the oxidation-chlorination step with a compound of the formula II:

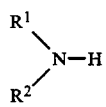

wherein $R^1$ and $R^2$ are individually selected from the group consisting of hydrogen, alkyl, alkoxy, cycloalkyl, cyanoalkyl, alkoxyalkyl, alkenyl and alkynyl wherein the alkyl, alkenyl and alkynyl moieties contain from one to six carbon atoms; and heterocyclic structures in which $R^1$ and $R^2$ together form an alkylene or oxyalkylene chain with two to five carbon atoms; and thereafter isolating the product, the improvement comprising:

(i) performing the oxidative-chlorination step (a) by simultaneously introducing into an aqueous solution of an acid and an inorganic salt, chlorine and an aqueous solution of a metal salt of a compound of formula I in a molar ratio of chlorine to the metal salt of said compound of formula I of from about 2 to 5 at from −30° C. to 30° C.; and (ii) purging the excess chlorine from the reaction mixture prior to reaytion step (b).

3. A process according to claim 2 wherein said metal salt of a compound of formula I is formed by dissolving the compound of formula I in sodium hydroxide.

4. A process according to claim 1 wherein said aqueous acid and inorganic salt solution comprises:
ten (10) parts water;
from about 0.5 to about 1.5 parts acid; and
from about 1 to 4 parts inorganic salt.

5. A process according to claim 1 wherein said chlorine is introduced as a gas at from about 2.0 to about 5.0 molar equivalents per mole of said compound of formula I.

6. A process according to claim 5 wherein said chlorine is introduced as a gas at from about 2.8 to about 3.8 molar equivalents per mole of said compound of formula I.

7. A process according to claim 1 wherein the oxidative chlorination takes place at from about −12° C. to about 5° C.

8. A process according to claim 1 wherein the compound of formula I is 2-mercapto-5-methylamino-1,3,4-thiadiazole.

9. A process according to claim 8 wherein the compound of formula II is dimethylamine.

10. A process for the production of 2-methylamino-1,3,4-thiadiazole-5-N,N-dimethylsulfonamide which comprises:
oxidatively chlorinating 2-mercapto-5-methylamino-1,3,4-thiadiazole by simultaneously introducing into a solution comprising:
ten (10) parts water;
from 0.5 to about 1.5 parts HCl; and
from about 1 to about 4 parts NaCl;
an aqueous solution containing one molar equivalent of the sodium salt of 2-mercapto-5-methylamino-1,3,4-thiadiazole and from about 2.8 to about 3.8 molar equivalents of chlorine;
at from about −12° C. to about 5° C.;
purging the excess chlorine from the reaction mixture with nitrogen;
reacting the sulfonyl chloride formed in the oxidative-chlorinating step with from about 7 to about 9 molar equivalents of dimethylamine; and isolating the product.

11. A process according to claim 2 wherein said chlorine is introduced as a gas at from about 2.0 to about 5.0 molar equivalents per mole of thiadiazole.

12. A process according to claim 11 wherein said chlorine is introduced as a gas at from about 2.8 to about 3.8 molar equivalents per mole of thiadiazole.

13. A process according to claim 2 wherein the oxidative chlorination takes place at from about −12° C. to about 5° C.

14. A process according to claim 2 wherein the compound of formula I is 2-mercapto-5-methylamino-1,3,4-thiadiazole.

15. A process according to claim 14 wherein the compound of formula II is dimethylamine.

16. A process for the production of 5-[[[(dimethylamino)carbonyl]methylamino]-N,N-dimethyl-1,3,4-thiadiazole-2-sulfonamide which comprises:
oxidatively chlorinating 2-mercapto-5-methylamino-1,3,4-thiadiazole by simultaneously introducing into a solution comprising
ten (10) parts water,
from about 0.5 to about 1.5 parts HCl, and
from about 1 to about 4 parts NaCl;
an aqueous solution containing one molar equivalent of the sodium salt of 2-mercapto-5-methylamino-1,3,4-thiadiazole and from about 2.8 to about 3.8 molar equivalents of chlorine;
at from about −12° C. to about 5° C.;
purging the excess chlorine from the reaction mixture with nitrogen;
reacting the sulfonyl chloride formed in the oxidative chlorination step with from about 7 to about 9 molar equivalents of dimethylamine;
reacting the 2-methylamino-1,3,4-thiadiazole-5-N,N-dimethylsulfonamide so formed with phosgene and dimethylamine; and
isolating the product.

* * * * *

UNITED STATES PATENT AND TRADEMARK OFFICE
CERTIFICATE OF CORRECTION

PATENT NO. : 4,562,260

DATED : December 31, 1985

INVENTOR(S) : Roger L. McDaniel, Jr., Jeffrey W. Portzer, Edward J. Zaiko

It is certified that error appears in the above-identified patent and that said Letters Patent is hereby corrected as shown below:

Column 11, line 9, following "mixture prior to", delete "reaytion" and substitute therefor -- reaction --.

Signed and Sealed this

Thirteenth Day of May 1986

[SEAL]

Attest:

DONALD J. QUIGG

Attesting Officer

Commissioner of Patents and Trademarks